(12) United States Patent
Tate et al.

(10) Patent No.: US 11,848,110 B2
(45) Date of Patent: *Dec. 19, 2023

(54) SECURE PATIENT MESSAGING

(71) Applicant: CVS Pharmacy, Inc., Woonsocket, RI (US)

(72) Inventors: Bryan D. Tate, Warwick, RI (US); Christine C. Sawicki, Marlborough, MA (US)

(73) Assignee: CVS Pharmacy, Inc., Woonsocket, RI (US)

( * ) Notice: Subject to any disclaimer, the term of this patent is extended or adjusted under 35 U.S.C. 154(b) by 53 days.

This patent is subject to a terminal disclaimer.

(21) Appl. No.: 17/839,033

(22) Filed: Jun. 13, 2022

(65) Prior Publication Data

US 2022/0319722 A1 Oct. 6, 2022

Related U.S. Application Data

(63) Continuation of application No. 15/959,851, filed on Apr. 23, 2018, now Pat. No. 11,387,005.

(Continued)

(51) Int. Cl.
*G16H 10/60* (2018.01)
*G16H 80/00* (2018.01)
*G06F 21/62* (2013.01)
*H04L 51/063* (2022.01)
*G06Q 40/08* (2012.01)
*G06N 20/00* (2019.01)

(Continued)

(52) U.S. Cl.
CPC ......... *G16H 80/00* (2018.01); *G06F 21/6245* (2013.01); *G06N 20/00* (2019.01); *G06Q 40/08* (2013.01); *G16H 10/60* (2018.01);

*H04L 51/063* (2013.01); *H04L 51/214* (2022.05); *G16H 20/10* (2018.01)

(58) Field of Classification Search
CPC .... G06N 20/00; G06F 21/6245; G06Q 40/08; H04L 51/063; G04L 51/14
See application file for complete search history.

(56) References Cited

U.S. PATENT DOCUMENTS

2003/0028399 A1  2/2003 Davis et al.
2011/0071868 A1  3/2011 Parker et al.
(Continued)

FOREIGN PATENT DOCUMENTS

WO  2016/110500  7/2016

OTHER PUBLICATIONS

International Search Report and Written Opinion for International Application No. PCT/US2018/028904, dated Sep. 12, 2018, 15 pgs.

*Primary Examiner* — Robert A Sorey
(74) *Attorney, Agent, or Firm* — PATENT LAW WORKS LLP

(57) ABSTRACT

The techniques described in this disclosure relate to methods and systems for generating a model profile to identify opportunities to, for example, initiate dialogue between a pharmacy and a patient. The techniques include a method comprising generating a model profile to identify at least one discrete opportunity to initiate dialogue with a patient; analyzing a patient profile associated with a patient to determine whether the patient profile fits the model profile; determining that the patient profile fits the model profile; and sending a message to the patient.

20 Claims, 10 Drawing Sheets

Related U.S. Application Data

(60) Provisional application No. 62/488,705, filed on Apr. 21, 2017.

(51) Int. Cl.
*H04L 51/214* (2022.01)
*G16H 20/10* (2018.01)

(56) References Cited

U.S. PATENT DOCUMENTS

| | | |
|---|---|---|
| 2011/0178820 A1 | 7/2011 | Soni et al. |
| 2012/0278101 A1 | 11/2012 | Howchowdhury et al. |
| 2016/0321406 A1 | 11/2016 | Timmerman et al. |
| 2017/0213005 A1 | 7/2017 | Cox et al. |
| 2017/0235894 A1 | 8/2017 | Cox et al. |
| 2017/0262445 A1 | 9/2017 | Jeon et al. |
| 2017/0351820 A1 | 12/2017 | Van Halteren et al. |
| 2018/0061077 A1* | 3/2018 | Grimm .................. G16H 10/40 |
| 2018/0063265 A1 | 3/2018 | Crossley et al. |
| 2018/0315490 A1* | 11/2018 | Jaruzel, II .............. G16H 10/60 |

\* cited by examiner

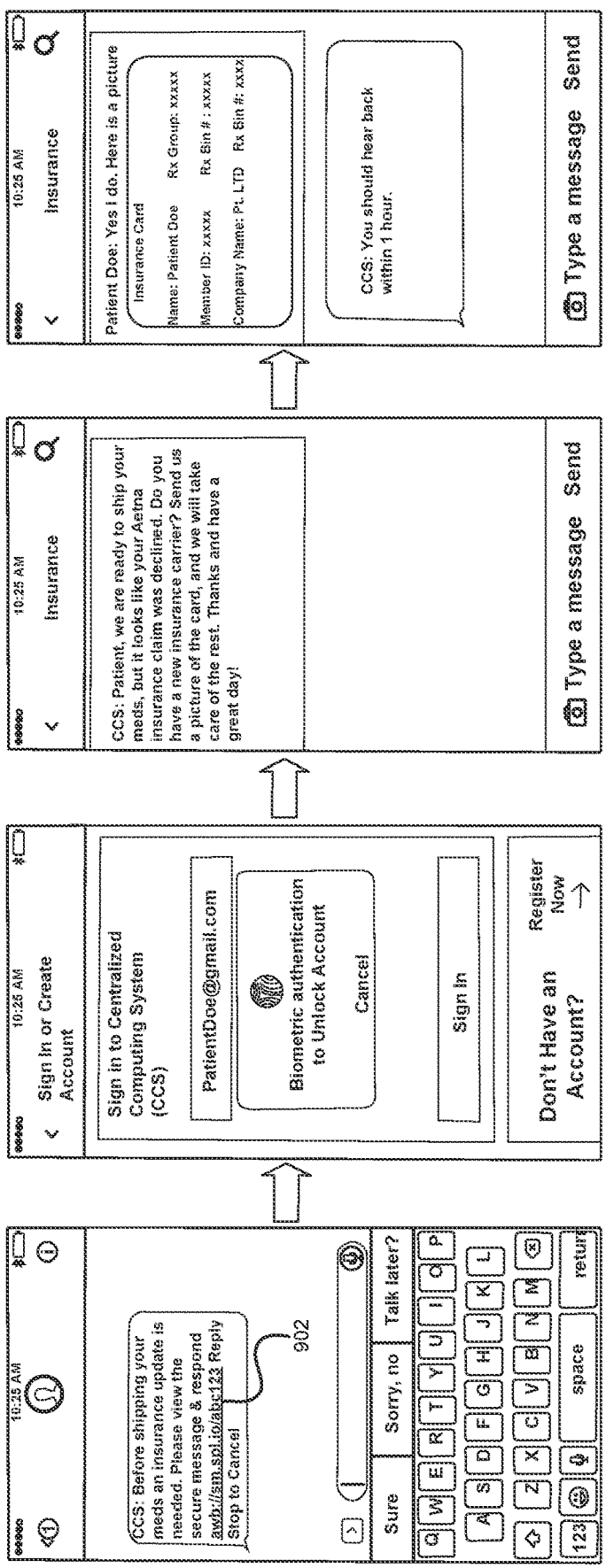

| | Patient ID | Phone Number | Message | Campaign ID |
|---|---|---|---|---|
| 1 | | | | |
| 2 | 12345678 | 1312345678 | CCS: We are concerned that you have not filled one of your meds recently. Can we help? Respond 1 = Yes, call me, 2 = 1 don't take it anymore or tap here ccs://sm.splio/abc12 to ask a question | MHA1232_Recapture_at1 |
| 3 | 13345678 | 1313345678 | CCS: Before shipping your meds an insurance update is needed. Please view the secure message & respond awb:// sm.splio/abc123 Reply Stop to Cancel | MHA1233_Recapture_at1 |
| 4 | 14345678 | 1314345678 | CCS: Your prescription is ready. Reply Stop to Cancel | MHA1234_Recapture_at1 |
| 5 | 15345678 | 1315345678 | CCS: Your next prescription is due to be refilled. Reply 1 to refill, 2 to cancel, Stop to stop receiving notices. prescription is ready. Reply Stop to Cancel | MHA12345_Recapture_at1 |
| 6 | 16345678 | 1316345678 | CCS: Authorize use of digital signature for online transactions via this link: ccs://sm.splio/signature_authorization. Reply Stop to Cancel | MHA12346_Recapture_at1 |
| 7 | 17345678 | 1317345678 | CCS: Click link to confirm change of address: ccs://sm.splio/address_change. Reply Stop to Cancel | MHA123457_Recapture_at1 |

Figure 10

SECURE PATIENT MESSAGING

CROSS-REFERENCE TO RELATED APPLICATIONS

This application is a continuation of U.S. patent application Ser. No. 15/959,851, titled "Secure Patient Messaging," filed on Apr. 23, 2018, which claims the benefit under 35 U.S.C. § 119(e) of U.S. Provisional Application No. 62/488,705, titled "Secure Patient Messaging," filed on Apr. 21, 2017, the entireties of both of which are hereby incorporated by reference.

Applicants hereby notify the USPTO that the claims of the present application are different from those of the parent application and any other related applications. Therefore, Applicants rescind any disclaimer of claim scope made in the parent application or any other predecessor application in relation to the present application. The Examiner is therefore advised that any such disclaimer and the cited reference that it was made to avoid may need to be revisited at this time. Furthermore, the Examiner is also reminded that any disclaimer made in the present application should not be read into or against the parent application or any other related application.

FIELD OF INVENTION

The present disclosure relates to secure and/or unsecure patient messaging. In particular, the present disclosure relates to a pharmacy engaging patients regarding medication in a secure and/or unsecure conversation anytime and anywhere.

BACKGROUND

Many health care providers/health care institutions (e.g., pharmacies, health centers, etc.) interact with customers (e.g., patients, etc.) to provide products and services. In interacting with customers, most health institutions seek ways to engage their customers in order to improve the delivery of their products and services.

Evolving technology trends and patient preferences call for integrating new technologies into the existing communication infrastructure of health care providers or institutions to enhance their communication with customers. For instance, a number of health care institutions currently communicate with customers using conventional techniques such as email, short message service (SMS), or phone calls without assessing optimal ways to use these tools based on patient preferences, relevant available customer data, etc.

Furthermore, most health care institutions fail to anticipate customer needs and appropriately communicate in a manner that not only engages customers but also improves health and wellbeing and enhances customer retention. This is largely because these health care institutions do not have or leverage customer data (e.g., customer expense data, customer health data, other behavioral data of customer, etc.) to determine efficient ways to communicate with and engage customers.

SUMMARY

The present disclosure relates to secure and/or unsecure patient messaging. In particular, the present disclosure relates to a pharmacy engaging patients regarding medication in a secure and/or unsecure conversation anytime and anywhere. The messaging session may be initiated by a patient, a centralized computing system associated with a health care institution (e.g., pharmacy), or a third-party contributor.

One innovative aspect of the subject matter described in this disclosure may be embodied in a computer-implemented method comprising generating a model profile, by a centralized computing system, the model profile being associated with a message type to identify at least one discrete opportunity to initiate dialogue with a patient; analyzing, by the centralized computing system, a patient profile associated with the patient to determine whether the patient profile fits the model profile; in response to determining that the patient profile fits the model profile, queuing, by the centralized computing system a message corresponding to the message type; sending the message to the patient; and adapting the model profile based on one or more of a patient response and other patient data stored in association with the patient profile.

Additionally, the message sent to the patient may be one of at least a portion of a one-way unsecure communication with the patient; and at least a portion of a two-way unsecure communication with the patient. The message could also be one of at least a portion of a two-way secure communication with the patient including a question from the patient; and at least a portion of a two-way secure communication with the patient including a request for health sensitive data associated with the patient.

Moreover, the centralized computing system may authenticate the patient based on a response from the patient. The centralized computing system may further adapt the model profile based on a response from the patient by generating an evaluation of a content and context of the response from the patient; and incorporating the evaluation into adapting the model profile to identify another discrete opportunity to initiate dialogue with the patient. The model profile may be generated based on one or more patient factors comprising one or more of a demographic factor describing a particular class of patients with shared characteristics to which the patient belongs to; a medication intake factor derived from prescription information of the patient; a diagnosis factor describing a cause and nature of a medical condition associated with the patient; an insurance factor derived from health insurance information associated with the patient; a clinical interaction factor describing a nature of historical interactions between the patient and a care team associated with the centralized computing system; a digital interaction factor describing a digital footprint of interactions between the patient and the centralized computing system; a retail purchase history factor associated with the patient; a payment history factor describing one or more sources of payment associated with prescription purchases of the patient; and a health record factor describing a medical history of the patient.

The centralized computing system may further apply machine learning to the one or more patient factors in generating the model profile and may further apply branching and conditional data analysis to a patient response to send a subsequent message to the patient. Additionally, the centralized computing system may adapt the model profile based on third-party data in one embodiment, the third-party data including captured health data associated with the patient.

Other implementations of one or more of these aspects include corresponding systems, apparatus, and computer programs, configured to perform the actions of the methods, encoded on computer storage devices.

BRIEF DESCRIPTION OF THE DRAWINGS

The present disclosure is illustrated by way of example, and not by way of limitation in the figures of the accompanying drawings in which like reference numerals are used to refer to similar elements.

FIGS. 9A-9D show an example flow for authenticating and communicating sensitive information between the patient and the centralized computing system, according to the techniques described herein.

FIG. 10 is an example aggregate of queued messages to be sent to a plurality of patients, according to the techniques described herein.

DETAILED DESCRIPTION

Figure 1:
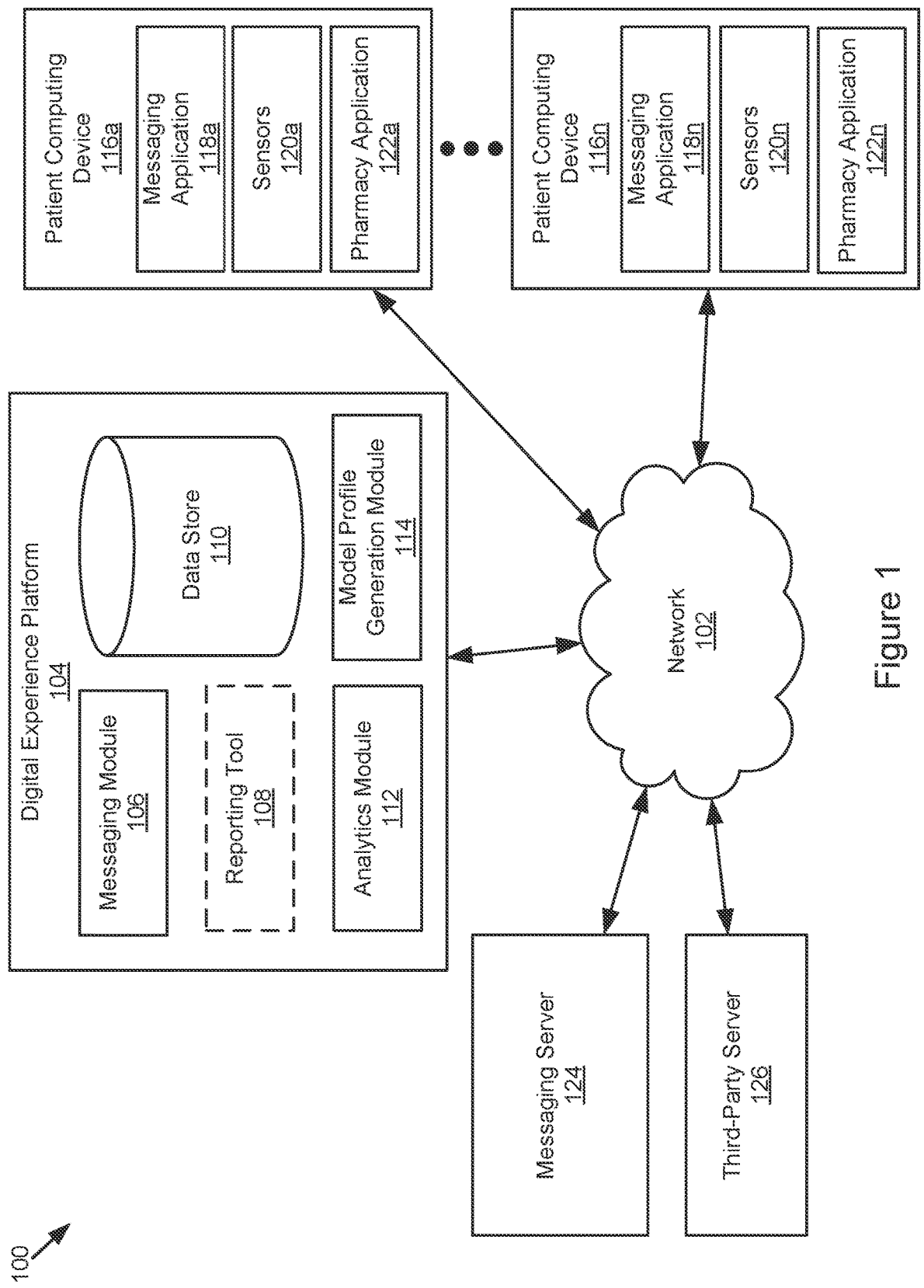
FIG. 1 is a high-level block diagram illustrating an example system in which a digital experience platform may be implemented, according to the techniques described herein.

Systems and methods for generating a model profile and sending a message to a patient based on the model profile are described below. While the systems and methods of the present disclosure are described in the context of a particular system architecture, it should be understood that the systems and methods can be applied to other architectures and organizations of hardware.

As set forth below, the technology described herein provides an innovative approach to messaging between a pharmacy and a patient. Time-relevant messages may be sent to a patient to develop and build the patient's health literacy. The messages may be created/distributed, for example, based on:
  i. Patient profile information, including:
    1. Patient demographic information
    2. Behavior/Plan/Insurance of the patient
  ii. Patient clinical information, including:
    1. Clinical interactions between the patient and care team
    2. Diagnosis/Condition of the patient
    3. Symptoms, notes, or healthcare events logged by the patient
    4. Drugs associated with patient prescription data
  iii. Patient/health care institution communications, including:
    1. Digital interactions between the patient and a health care institution
    2. Payment data of the patient
    3. Interactions between patient and an automated messaging service These techniques further include combining a clinical and coverage profile of the patient to create discrete opportunities that currently do not exist. The techniques further include branching and conditional data analysis to identify messaging opportunities based on a patient's risk profile.

Automatic opportunity identification to engage the patient may also be based on the patient's self-identification of need or support. The techniques include the ability to understand the need behind the patient response and to automatically identify opportunities and push messages/content based on the patient's need by mapping response types to the specific content sent to the patient from the digital experience platform.

The techniques further include multi-party initiation of persistent conversations within a single hub. For example, the techniques introduced here include multi-organizational messaging platforms where any party (e.g., patient, physician, caregiver, pharmacy, etc.) can initiate a conversation with one or more other parties in a secure channel. This is beneficial because healthcare decisions are rarely between two parties. For example, a medication decision may be made among multiple parties (e.g., patients, providers, payers, pharmacy plans, etc.). The techniques connect all of these through a single messaging solution that is Health Insurance Portability and Accountability Act (HIPAA) compliant where any party can initiate a secure conversation with another.

The techniques further include automatic generation and sending of relevant non-secure messages and continuing with secure content after authentication of the patient. For example, the techniques may include a custom call to action based on operations/prescriber actions. In healthcare, this unique mix meets patient expectations such that communication is handled digitally and meets HIPAA requirements for security in a single solution.

FIG. 1 is a high-level block diagram illustrating an example system 100 in which a digital experience platform 104 may be implemented. The system 100 includes a digital experience platform (DEP) 104, clients 116a ... 116n, a messaging server 124 and a third-party server 126. The network 102 may communicatively couple the various components of the system 100.

The DEP 104 may be configured to generate a model profile, analyze a patient profile in order to fit the model profile to the patient profile, and identify opportunities to engage the patient (e.g., initiate dialogue with the patient). In some embodiments, the DEP 104 may include a messaging module 106, a reporting tool 108, a data store 110, an analytics module 112, and a model profile generation module 114. The various components of the DEP 104 are further discussed with reference to FIG. 2.

The patient computing devices 116a ... 116n (simply referred to as patient computing device 116) may be configured to receive secure and/or unsecure messages via the network 102, receive one or more inputs from a patient, and send a response via the network 102 to the DEP 104 and other components of the system 100. In one embodiment, the patient computing device 116 includes a messaging application 118, one or more sensors 120, and a pharmacy application 122. These components of the patient computing device 116 are further discussed with reference to FIG. 3.

The messaging server 124 may be a computing device having a Short Message Service (SMS) gateway configured for receiving and sending SMS transmissions to and/or from components coupled to the network 102. In essence, the messaging server 124 may, for example, receive and/or rout messages or messaging opportunities via the network 102 between the patient computing device 116 (using either the messaging application 118 and/or the pharmacy application 122), the DEP 104, insurance provider systems (not shown), electronic health record (EHR) systems (not shown), etc. While the messaging server 124 may be described in the context of SMS transmissions, it should be understood that the messaging server 124 may also be configured to operate using other message transmissions such as email, mobile push messaging, embedded messaging, other third-party messaging services, etc.

The third-party server 126 of FIG. 1 may be configured to process and store third-party data such as health information relevant to optimizing/improving generating the model profile. This health information may include data extracted from the one or more sensors 120 of the patient computing device, data from medical devices (e.g., smart pacemakers, smart blood pressure monitors, smart glucometer, etc.) associated with the patient, electronic health records (e.g., EHR) of the patient from health care institutions (e.g., hospitals), patient reported health events, etc.

As noted above, the network 102 may be configured for communicatively coupling the various components of the system 100. In one embodiment, the network 102 may be wired or wireless, and may have numerous different configurations. Furthermore, the network 102 may include a local area network (LAN), a wide area network (WAN) (e.g., the internet), and/or other interconnected data paths across which multiple devices (e.g., third-party server 126, patient computing device 116, messaging server 124, DEP 104, etc.) may communicate. In some embodiments, the network 102 may be a peer-to-peer network. The network 102 may also be coupled with portions of a telecommunications network for sending data using a variety of different communication protocols. In some embodiments, the network 102 may include Bluetooth (or Bluetooth low energy) communication networks or a cellular communications network for sending and receiving data including via short messaging service (SMS), multimedia messaging service (MMS), hypertext transfer protocol (HTTP), direct data connection, WAP, email, etc. Although the example of FIG. 1 illustrates one network 102, in practice one or more networks 102 can connect the entities of the system 100.

Figure 2:
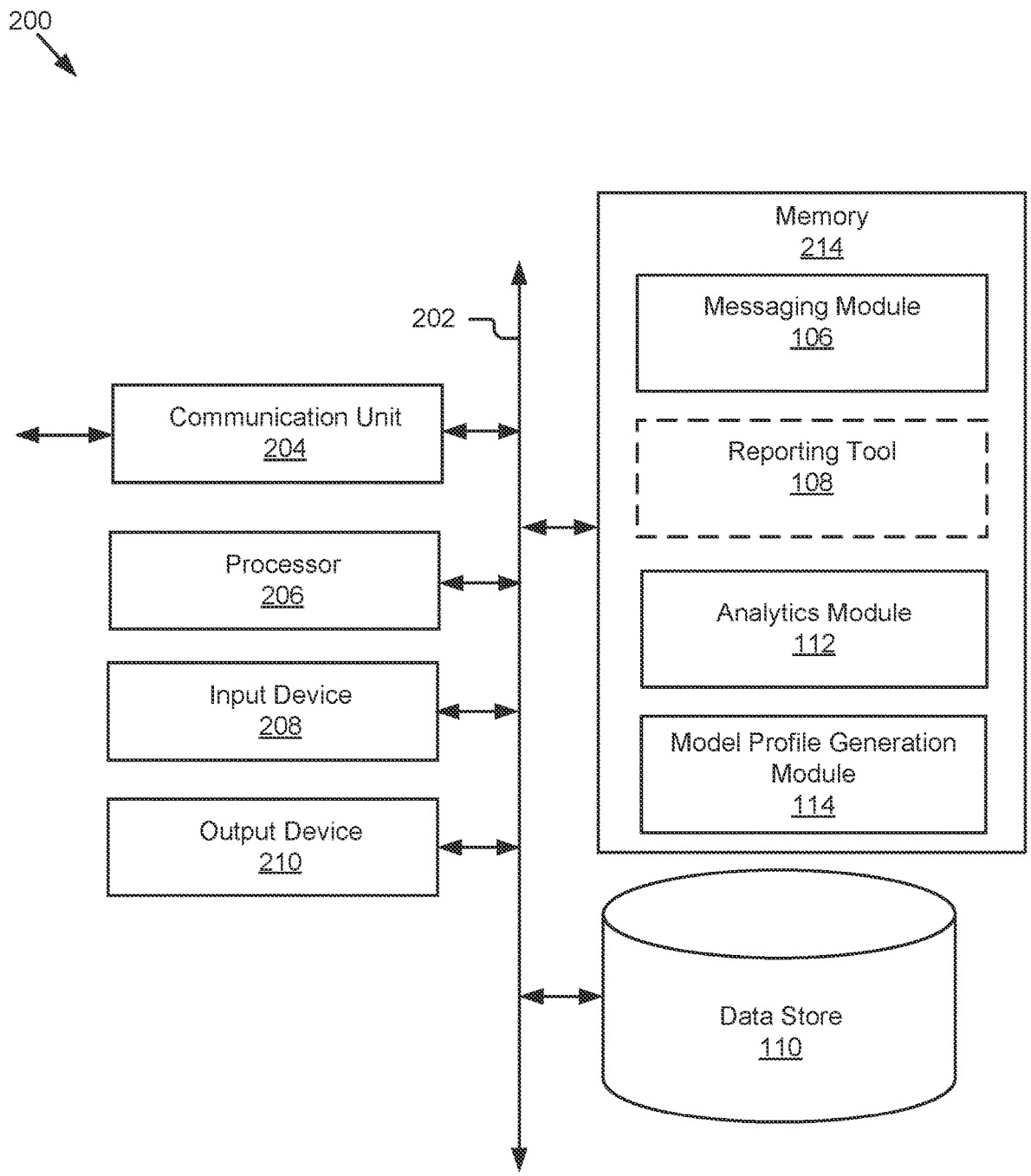
FIG. 2 is a block diagram illustrating an example computing system on which the digital experience platform may be implemented, according to the techniques described herein.

FIG. 2 is a block diagram illustrating an example computing system 200 (also called centralized computing system (CCS)) on which the digital experience platform may be implemented. The computing system 200 may include memory 214, a data store 110, a communication unit 204, a processor 206, an input device 208, and an output device 210. As shown, the bus 202 may couple the various components of the computing system 200

The memory 214 may store instructions and/or data that may be executed by the processor 206. In the illustrated implementation, the memory 214 includes a messaging module 106, a reporting tool 108, an analytics module 112, and a model profile generation module 114 of the DEP 104.

The messaging module 106 may be configured to transmit one or more messages from the DEP 104 to a patient computing device 116. In some embodiments, the messaging module 106 may receive and process one or more responses received from the patient computing device 116. For instance, the messaging module 106 may identify and/or compose one or more messages from the data store 110 based on the model profile, and/or new analysis performed by the analytics module 112. Following this, the messaging module 106 may transmit the one or more messages to one or more patients.

The reporting tool 108 shown residing in memory 214 may be an application that evaluates the efficacy of the operations performed by components of the DEP 104. For instance, the reporting tool 108 may generate a report that may be used to reconfigure the system 100 for optimal performance. These reports may, for example, include a report showing the effectiveness of one model profile relative to another model profile in effectively engaging a particular patient or a set of patients, etc.

The analytics module 112 of FIG. 2 may be configured to analyze and/or operate on one or more parameters including patient profile factors (e.g., patient factors such as a demographic factor, patient behavior factors, patient insurance plan factor, etc.), patient clinical factors (e.g., medication intake factor, diagnosis factor, health condition factor, symptoms, notes, or healthcare events logged by the patient, prescription drug factors), and patient/health care institution communication factors (e.g., patient interaction with a clinical or non-clinical care team, retail purchase history factor, payment history factor, patient interaction with an automated messaging service, etc.) associated with a patient to produce a profile result useable by the model profile generation module to generate the model profile. As used herein, the model profile may represent a proposed patient profile or a construct patient profile generated by the model profile generation module 114 to facilitate optimally identifying opportunities to initiate and/or engage in having one or more dialogues with a patient. In some embodiments, the model profile generation module 114 may generate and maintain multiple model profiles corresponding to different opportunities to initiate and/or engage with a patient. For example, the model profile generation module 114 may generate and maintain a model profile for a patient having frequent interaction with a pharmacy (e.g., a diabetes patient with monthly medication and testing needs) and a second model profile for patients having less frequent interaction with the pharmacy. It should be understood that any number of model profiles may be generated and maintained by the model profile generation module 114.

The analytics module 112 may apply one or more rules, logic, and/or appropriate operations to the one or more parameters, with or without patient responses, to produce the profile result which may be used by the model profile generation module 114 to generate the model profile and/or adapt the model profile. In some embodiments, the analytics module 112 may identify statistical patterns within the one or more parameters based on results produced by analyzing and operating on one or more parameters. These statistical patterns may be used by the model profile generation module 114 to generate and/or adapt the model profile. In other embodiments, the analytics module 112 may apply machine learning techniques (e.g., Q-learning, Naïve Bayes Classifier Algorithm, K-Means Clustering Algorithm, Support Vector Machine Algorithm, Linear Regression, Logistic Regression, Artificial Neural Networks, Random Forests, Decision Trees, Nearest Neighbors, etc.) to the one or more parameters and/or other data in order to produce the profile result. In some embodiments, the analytics module 112 may further incorporate other data from sensors 120 of the patient computing device 116, data from the third-party server 126, etc., in producing analysis that may be used for generating and/or adapting the model profile.

In some cases, the analytics module 112 may generate a health literacy score for a patient based on the patient's interaction with the system and/or the patients current behaviors tracked by the patient computing device 116 or a third-party service. The analytics module 112 may weight various factors in determining the health literacy score. For example, the patient/health care institution communications listed above may be weighted neutrally (e.g., assigned a weight of 1), the patient profile factors may be more heavily weighted (e.g., assigned a weight greater than 1), and the patient clinical factors may be weighted most heavily (e.g., assigned a weight greater than 2). In some embodiments, weights for individual factors with each of the above listed categories may be varied. It should be understood that the weighting listed above is an example and various weights may be assigned to the factors based on the intended target audience for the communications. In some embodiments, patient literacy scores of multiple patients may be used by the model profile generation module 114 to generate and/or adapt the model profile. This may be done in real-time as the data in the data store 110 evolves, so that messages can be properly tailored to patients in a timely manner.

In other embodiments, the analytics module may track the efficacy of messages by tracking correlations between the patient's interaction with the system and a particular health outcome. In some embodiments, the analytics module may track successful and/or unsuccessful outcomes based on messages sent to patients and the model profile generation module 114 may use the results to generate and/or adapt the model profile.

The data store 110 may be a non-transitory memory that stores data for providing the functionality described herein. In the illustrated embodiment, the data store 110 may be communicatively coupled to the bus 202 to receive data for storage and provide data for retrieval upon a request for the data. For instance, the data store 110 may be configured to store patient data in association with the patient profile, useable by the various modules of the DEP 104. For example, the data store 110 may store patient profile information such as a patient identification (ID), patient phone number, message ID, patient demographic data (e.g., address, contact preferences, diagnosis, pharmacy information), and other patient data such as the patient's risk profile, insurance data of the patient, sources of payment applied to prescription purchases of the patient (e.g., for medication X, 60% of the costs may be covered by the patient's insurance, 20% of the costs may be covered by the patient, and 10% of the costs may be covered by discounts, rebates, etc.), etc., which may be used by the analytics module 112 in producing the profile result. In other embodiments, the data store 110 may store a plurality of preconfigured messages that may be sent to the patient, and/customized messages that may be sent to the patient. In some cases, the data store may also store messages from the patient to the pharmacy. In such instances, the analytics module 112 may analyze the stored messages from the patient to the pharmacy, in conjunction with other relevant information stored on the data store 110, in order to produce the profile result for generating and/or updating the model profile.

The communication unit 204 may be hardware for receiving and transmitting data by linking the processor 206 to the network 102 and other components of system 100. The communication unit 204 may receive data for processing by processor 206. For example, the communication unit 204 may receive image and text data (e.g., FIG. 8) from a patient computing device 116 for processing by the messaging module 106 and/or the analytics module 112. The communication unit 204 may also transmit information (e.g., CCS message 804 of FIG. 8A) to the patient computing device 116 for display to a patient. In one embodiment, the communication unit 204 may include a port for direct physical connection to the network 102. In another embodiment, the communication unit 204 may include a wireless transceiver (not shown) for exchanging data with the patient computing device 116 or any other communication channel using one or more wireless communication methods, such as IEEE 802.11, IEEE 802.16, Bluetooth®, cellular communications, or another suitable wireless communication method.

The processor 206 may include an arithmetic logic unit, a microprocessor, a general-purpose controller, or some other processor array to perform computations and provide electronic display signals to a display device (e.g., display device coupled to the computing device 200, display device of the patient computing system 116, etc.). In some implementations, the processor 206 is a hardware processor having one or more processing cores. The processor 206 may be coupled to the bus 202 for communication with the other components of the computing system 200. Processor 206 may process data signals and may include various computing architectures including a complex instruction set computer (CISC) architecture, a reduced instruction set computer (RISC) architecture, or an architecture implementing a combination of instruction sets. Although only a single processor is shown in the example of FIG. 2, multiple processors and/or processing cores may be included. It should be understood that other processor configurations are herein contemplated.

The input device 208 (e.g., digital, and/or virtual keyboard, mouse, or the like) may be used by a user (e.g., pharmacist, sales clerk, etc.) to enter any relevant information into the example computing system 200. For instance, the messaging module may receive an operator input via the input device 208 and use the input to send a message to the user of the patient computing device 116. Similarly, the output device 210 (e.g., display device, printer, fax machine, or the like) may be used to generate any relevant outputs from the computing system 200.

Figure 3:
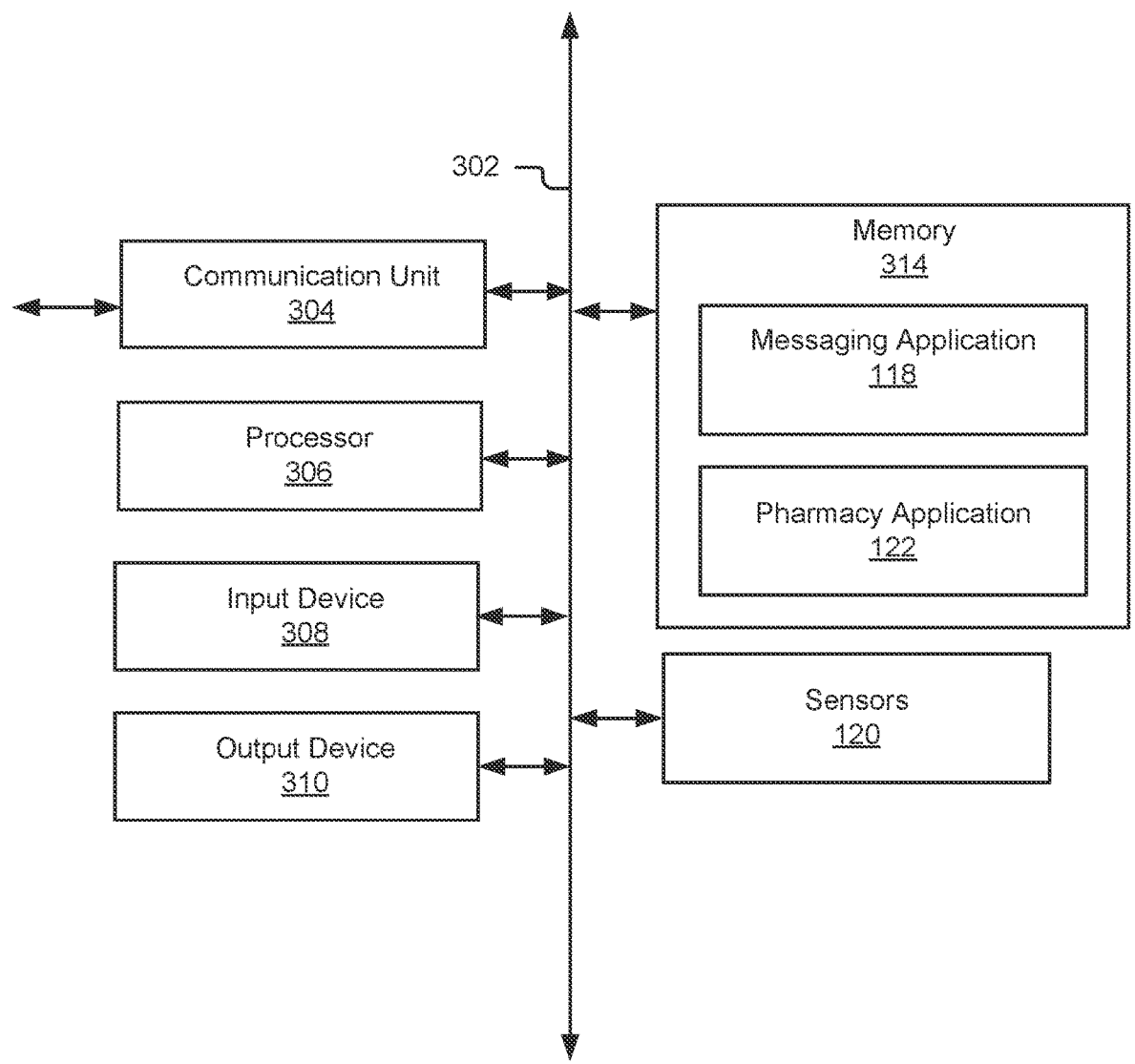
FIG. 3 is a block diagram illustrating an example patient computing device, according to the techniques described herein.

FIG. 3 is a block diagram illustrating an example patient computing device 116. In one embodiment, the patient computing device may include one or more memory 314 and one or more processors 306 coupled via a bus 302 to an input device 308, an output device 310, a communication unit 304, and one or more sensors 120. The patient computing device 116 may be, for example, a laptop computer, a desktop computer, a tablet computer, a mobile telephone, a personal digital assistant (PDA), a mobile email device, or any other electronic device capable of transmitting and receiving data.

The patient computing device 116 may store one or more instructions in the memory 314 that are executable by the processor 306. For instance, the memory 314 may store a messaging application 118 that facilitates receiving a message from the DEP 104 (e.g., via messaging server 124) and displaying the message on the output device 310 (e.g., display screen). The messaging application 118 may also receive inputs from the patient via the input device 308 (e.g., physical, and/or virtual keyboard) and may facilitate transmitting the received input from the patient to the DEP 104.

The patient computing device 116 may also execute an application (not shown) that may make storage requests (e.g., read, write, etc.) to storage devices coupled to the network 102. For instance, patient computing device 116 may include a health application that logs the data captured by the sensors 120 and transmits the logged data to the third-party server 126 for storage.

The memory may also store a pharmacy application 122 which is useable by the patient to purchase one or more products (e.g., medications, groceries, etc.). The pharmacy application 122 may further include other tools for tracking medication data associated with the patient (e.g., medication intake, questions regarding a prescription, etc.). The pharmacy application 122 may further be configured to provide for secure communication between a patient and the pharmacy. For example, in one embodiment, a message received by the patient, via the messaging application 118, may include a link that launches the pharmacy application 122 and authenticates the user prior to beginning a secure communication. In another embodiment, the link may launch a web browser on the patient computing device 116 that displays a web page for the pharmacy where the secure communication can take place.

The sensors 120 shown in FIG. 3 may include one or more sensors configured to detect relevant patient data such as (a) patient health data (e.g., patient heart rate, patient calorie intake tracking data, patient blood pressure data, patient's temperature, etc.), (b) patient behavior data (e.g., medication intake pattern of patient, treatment practices by patient, patient exercise data, etc.), and (c) environmental data (e.g., patient's geolocation, and/or conditions around which the patient lives such as weather, pollution density of environment around patient, nature of community within which patient resides, etc.). In some embodiments, various combinations of the one or more sensors 120 may be embedded or integrated with the patient computing device 116 and/or coupled with the patient computing device 116 via wired/wireless connectivity.

In some embodiments, the data captured by the sensors 120 may be transmitted via the communication unit to the third-party server 126 and/or the DEP 104. This captured data may be used by the DEP 104 to generate and/or adapt the model profile in order to improve identifying opportunities for initiating dialogue with the patient.

The processor 306 and the communication unit 304 shown in FIG. 3, perform functions similar to those discussed with reference to the processor 206 and communication unit 204 of FIG. 2.

Figure 4:
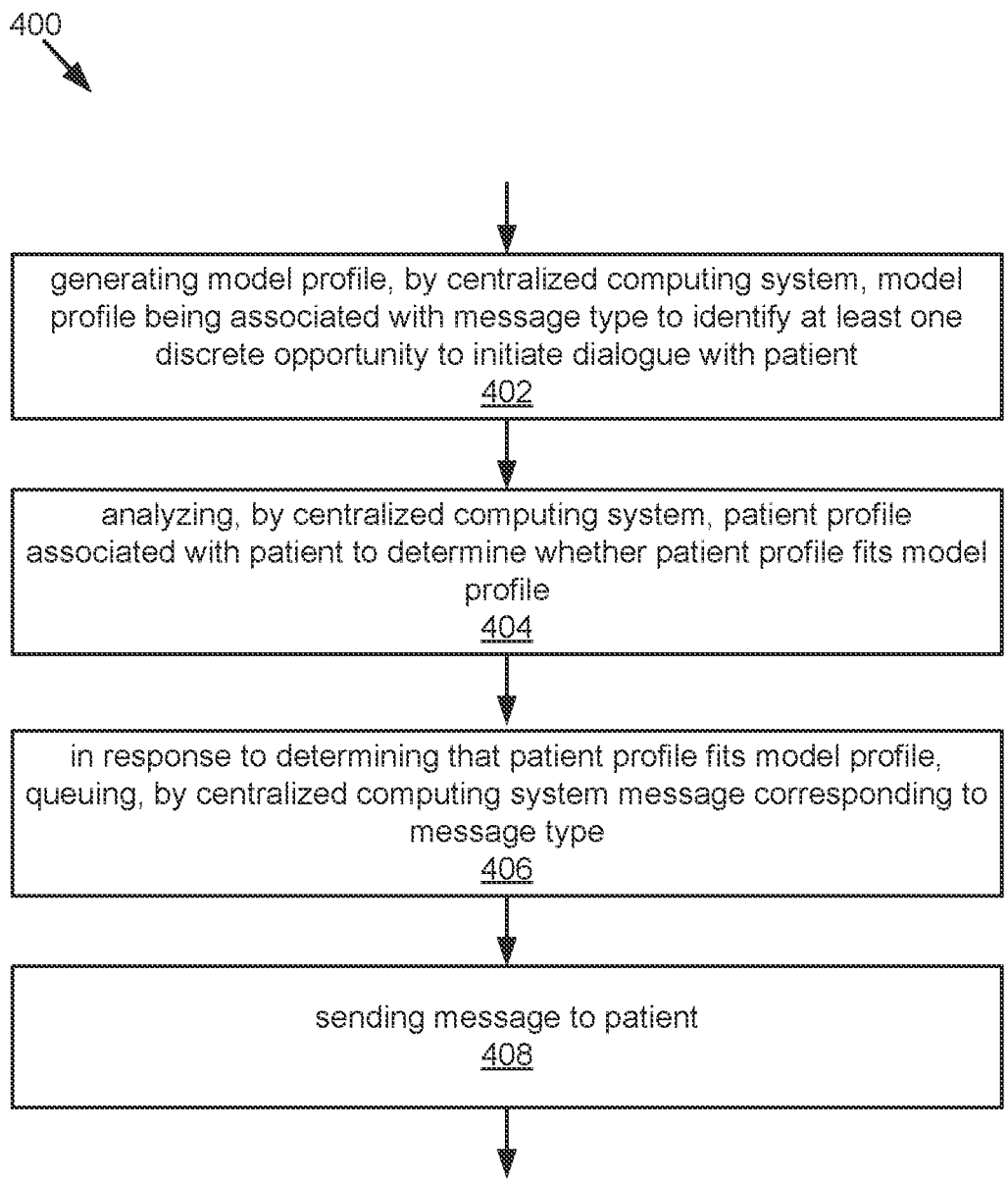
FIG. 4 is a flowchart of an example method for sending a message to a patient, according to the techniques described herein.

FIG. 4 is a flowchart of an example method for sending a message to a patient. At 402, the model profile generation module 114 generates a model profile which may be associated with a message type to identify at least one discrete opportunity to initiate dialogue with a patient. At block 404, the analytics module 112 may analyze a patient profile extracted from the data store 110, and/or the third party-server 126, to determine whether the patient profile fits the model profile. The analytics module 112 may analyze the patient profile by identifying patterns within the patient profile that match the model profile in order to select corresponding messages to send to a given patient whose patient profile fits the model profile.

In response to determining that the patient profile fits the model profile, the messaging module 106 queues a message at 406 which is subsequently sent to the patient at 408. In some embodiments, the messaging module 106 may send a single message in the message queue to a single patient. In other cases, the messaging module 106 may send a plurality of messages in the queue to a plurality of patients simultaneously. In some embodiments, the messaging module 106 may automatically send the messages without requiring any involvement of a DEP operator (e.g., pharmacist, sales clerk, etc.). In other embodiments, the messaging module 106 may be manually controlled by a DEP operator (e.g., pharmacist, sales clerk, etc.) to send the message to the patient.

Figure 5:
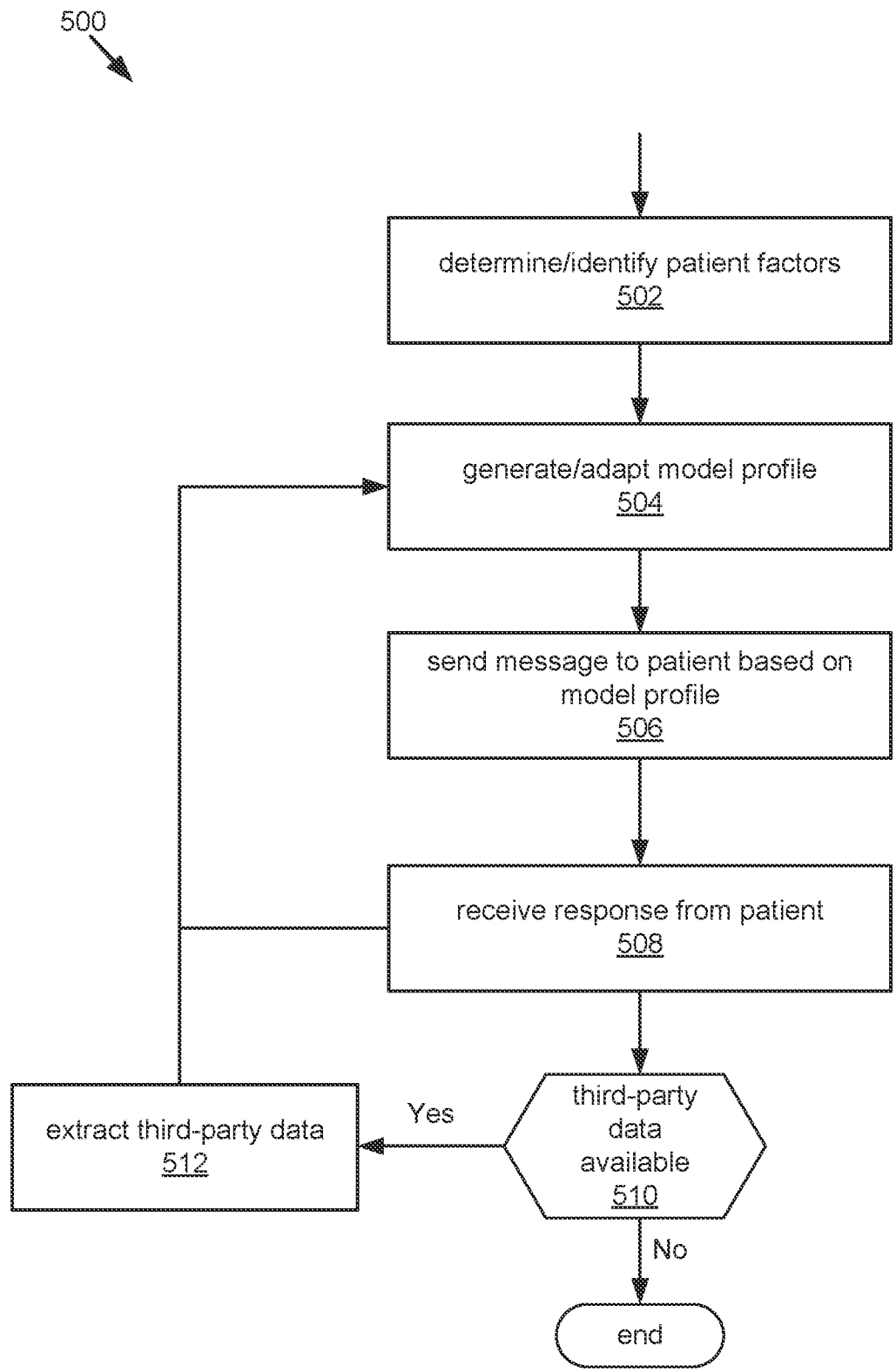
FIG. 5 is a flowchart of an example method for generating/updating the model profile, according to the techniques described herein.

FIG. 5 is a flowchart of an example method 500 for generating/updating the model profile. At 502, the analytics module 112 may determine/identify one or more patient factors such as: a demographic factor describing a particular class of patients with shared characteristics to which the patient belongs to; a medication intake factor derived from prescription information of the patient; a diagnosis factor describing a cause and nature of a medical condition associated with the patient; an insurance factor derived from health insurance information associated with the patient; a clinical interaction factor describing a nature of historical interactions between the patient and a care team associated with the centralized computing system; a digital interaction factor describing a digital footprint of interactions between the patient and the centralized computing system; a retail purchase history factor associated with the patient; a payment history factor describing one or more sources of payment associated with prescription purchases of the patient; and a health record factor describing a medical history of the patient.

At 504, the model profile generation module 114 may generate/adapt a model profile based on the analysis performed by the analytics module 112 from step 502. At 506 the messaging module 106 may send a message to the patient based on the model profile as noted above. The patient may in turn transmit a response using the messaging application 118. At 508, the messaging module 106 may receive the response from the patient. The response from the patient may be looped back into generating the model profile.

At 510, if third-party data (e.g., captured health data associated with the patient, such as data captured by sensors 120 on the patient computing device, or the like) is available, this third-party data may be extracted at 512 and incorporated at 504 into generating and/or adapting the model profile in order to improve the model profile for identifying opportunities to further engage the patient.

The process depicted in the flowcharts of FIGS. 4 and 5 may facilitate multiple types of message transmissions (e.g., SMS message transmissions) between a health care institution and a patient. In one embodiment, the message transmission may be a one-way message from the pharmacy to the patient without requiring any response from the patient. This message transmission type may be intended for informational purposes, such as providing status information to the patient (e.g., "one or more of your prescriptions are ready for pick up," "your medication has been shipped," "here are some anticipated side effects associated with medication X," etc.). In another embodiment, the message transmission may be a two-way message between the pharmacy and the patient. For instance, this two-way message transmission type may include a simple question to the patient (e.g., "confirm delivery date," "reply YES if you want to receive prescription reminders," "reply STOP if you want to stop receiving prescription reminders," adherence reminders, etc.).

In another embodiment, the message transmission may be initiated by the patient and include a two-way secure communication between the patient and the health care institution and/or third-party systems. This patient-initiated secure communication between the pharmacy and the patient may allow the patient to ask the pharmacy any health-related question involving sensitive information (e.g., "what are the procedures regarding taking medication X," "how can I manage the side effects of medication X," "How do I maintain medical device Y," "what are some healthy habits I can follow to improve my current condition," etc.). In other embodiments, the message transmission may be initiated by the pharmacy, and include a two-way secure communication between the pharmacy and the patient. In such instances, the two-way pharmacy-initiated secure communication may be intended to ask the patient any health-related question involving the transmission of sensitive health data (e.g., "Your insurance requires an update, tap link to provide relevant update information," "confirm co-pay change," etc.).

Figure 6B:
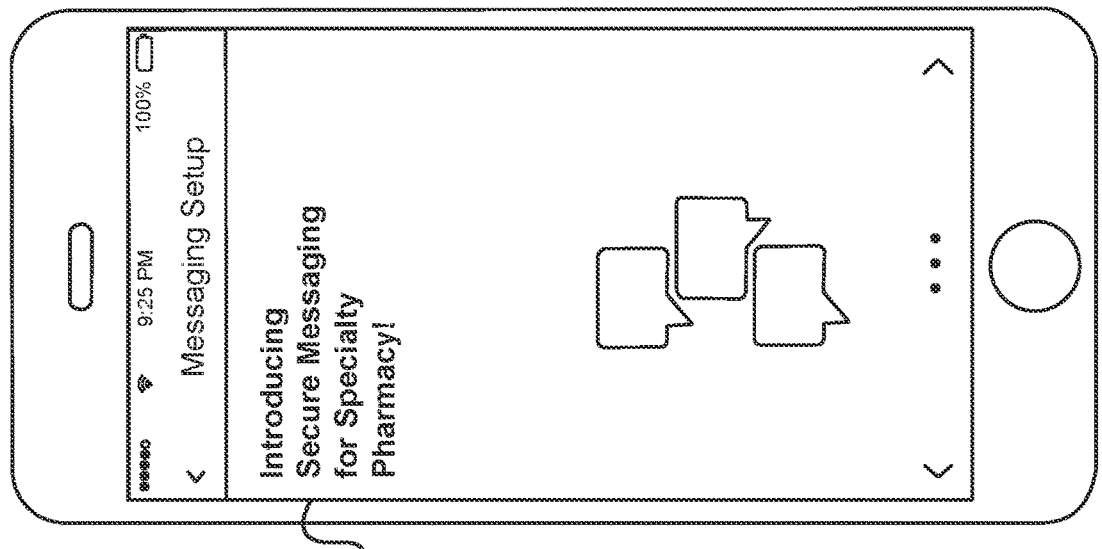
FIG. 6B shows an example message displayed on the display device 604 responsive to authenticating the patient, according to the techniques described herein.
Figure 6A:
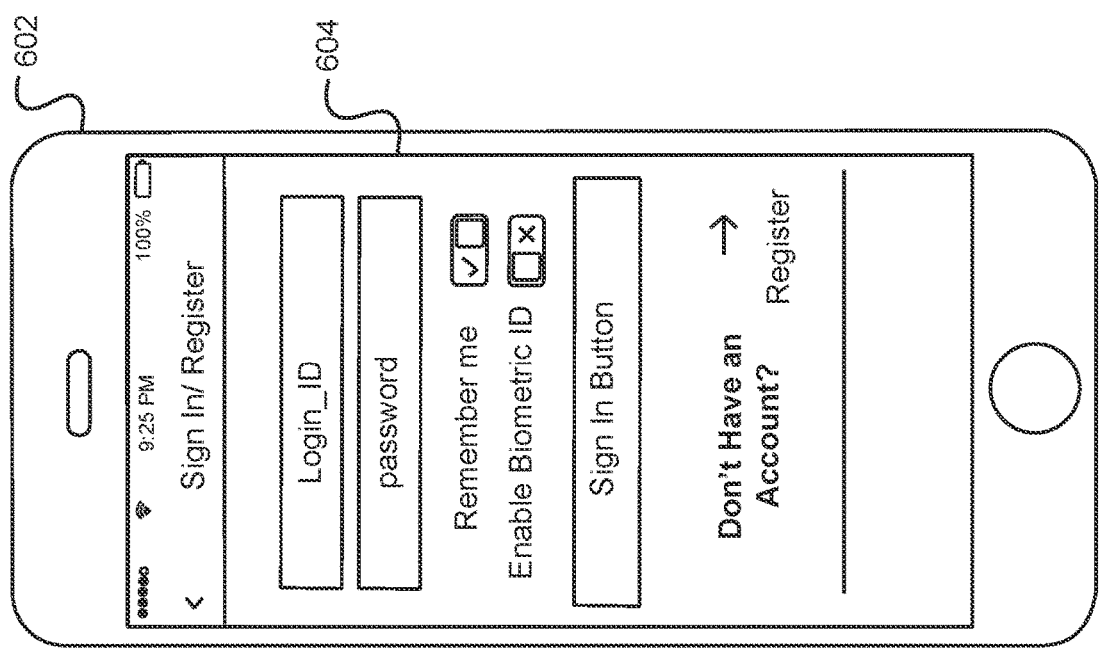
FIG. 6A is an example user interface on a display of an example patient computing device for accessing a pharmacy application on the patient computing device, according to the techniques described herein.

For the secure message transmissions discussed herein, the user (e.g., patient, physician, caregiver, pharmacy, etc.) may be provided a means of authentication to establish the secure connection between the pharmacy and the patient. For example, FIG. 6A shows an example user interface on a display of an example patient computing device 116 for accessing a pharmacy application on the patient computing device 116. As shown in the figure, the example patient computing device 116 may comprise a smart phone 602 having a display 604 on which the pharmacy application 122 may display a graphical user interface (GUI) that, for example, can provide a means for authenticating the patient (e.g., through the login screen shown in the figure). In some embodiments, the GUI on the display device 604 may be generated by the pharmacy application 122 responsive to the patient interacting with (e.g., clicking) content sent by the messaging module 106 of the DEP via the messaging application 118. FIG. 6B shows an example message displayed on the display device 604 responsive to the patient being authenticated.

Figure 7D:
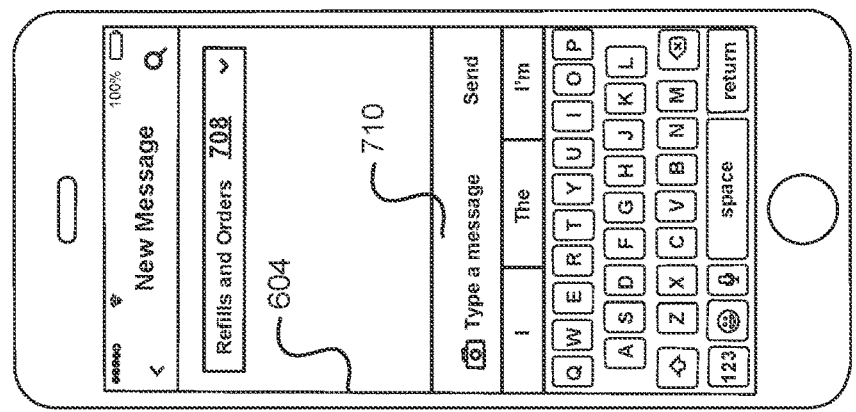
FIGS. 7A-7D show an example sequence for selecting an option associated with a menu on the example display device 604 of the patient computing device 116, according to the techniques described herein.
Figure 7C:
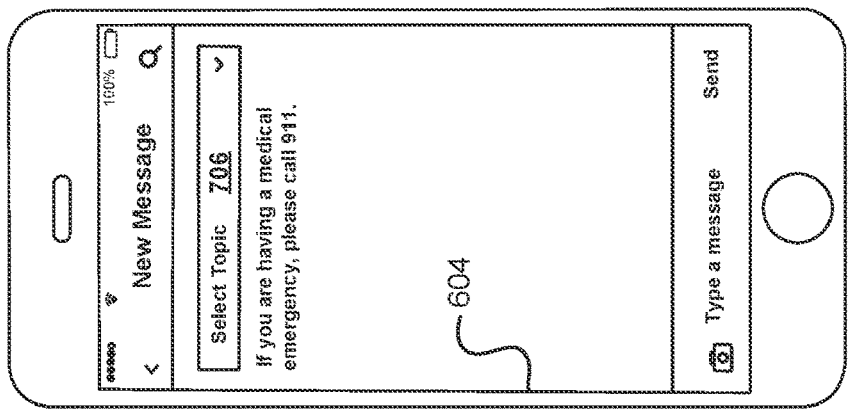

Once the user (e.g., patient, person acting on behalf of patient, guest, etc.) is granted access to the pharmacy application 122, the user may initiate a secure communication/dialogue with the health care institution (e.g., pharmacy), such as the patient-initiated secure communication discussed above. For example, the user may be presented with one or more menus/options for selecting a topic for the communication, obtaining information, etc. For instance, FIGS. 7A-7D show an example sequence for selecting an option associated with a menu on the example display 604 of the patient computing device 116. In FIG. 7A, the pharmacy application 122 displays two menus 704 and 706 associated with the secure messaging communication option 702. The two menus 704 and 706 may be displayed on the display 604 responsive to the user being authenticated. The user may select menu 704 to begin a secure communication with for example, a pharmacist. This menu selection by the user may be motivated by the user wanting to request information (e.g., prescription status information) from the pharmacist.

Figure 7B:
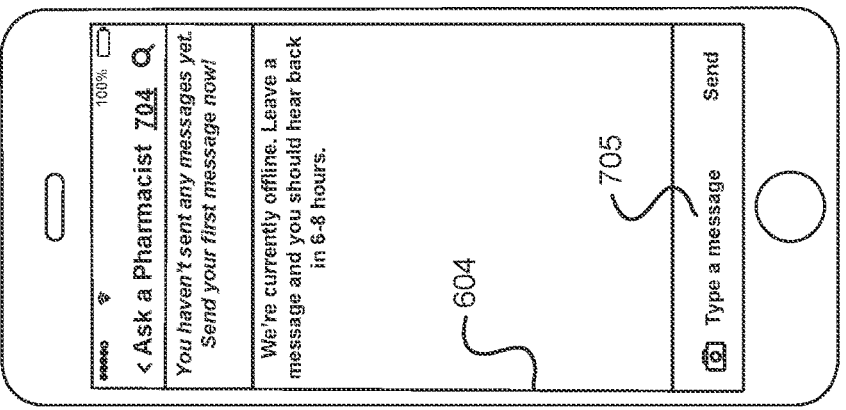
Figure 7A:
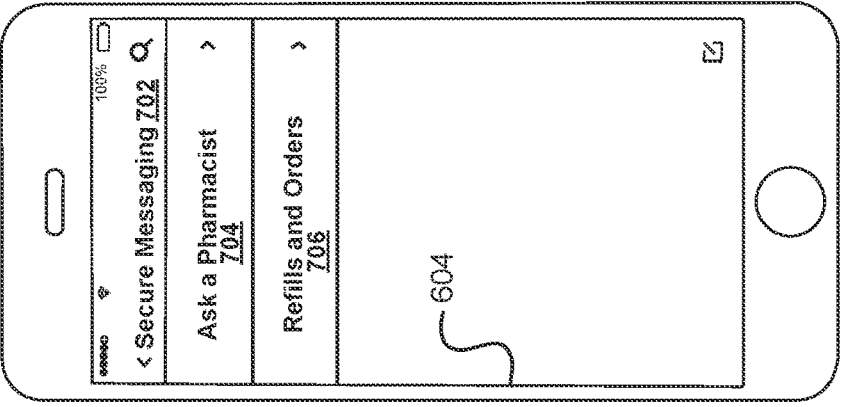

In FIG. 7B, a GUI may be displayed on the display 604 once the user selects menu 704. The user may begin composing a message by interacting with the "Type a message" element 705 displayed in the GUI. In response to the user interacting with the element 705, the GUI may transition from the example shown on the display device 604 of FIG. 7B to the GUI shown in FIG. 7C. As shown in FIG. 7C, the GUI may include a drop-down menu 706 that allows the user to select a topic for the message. In some embodiments, responsive to the user selecting a topic, a sub-topic menu 708 may be displayed, for example, as depicted in the example of FIG. 7D. The user may then proceed to type a message associated with the selection in the sub-topic from drop-down menu 708. The message may be displayed in the section 710 of the display 604.

Figure 8B:
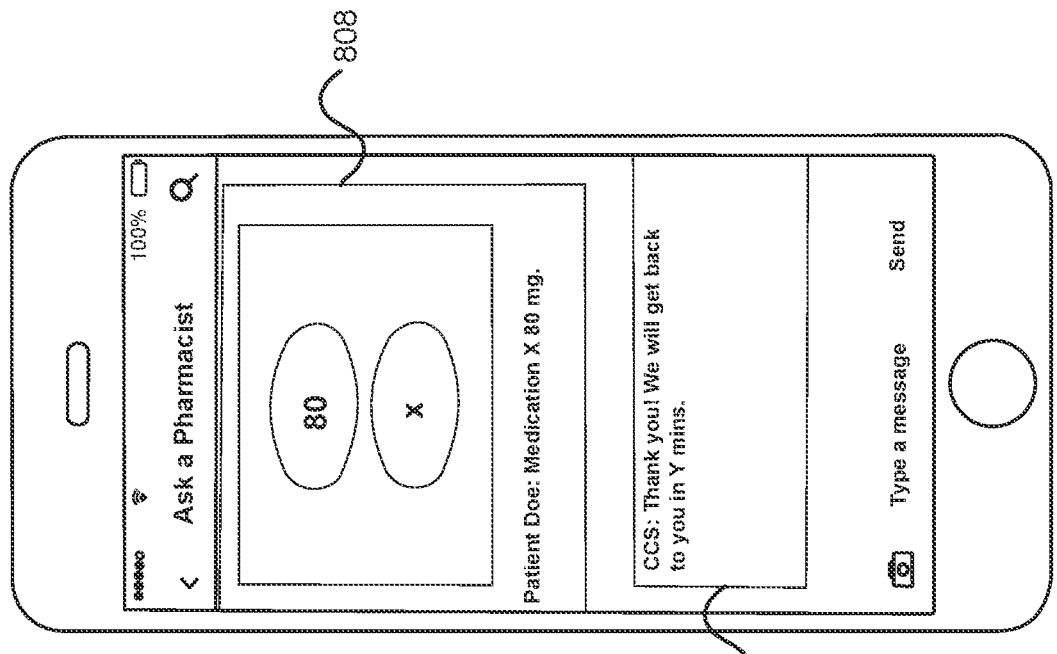
FIGS. 8A and 8B show an example messaging dialogue between the patient and the centralized computing system, according to the techniques described herein.
Figure 8A:
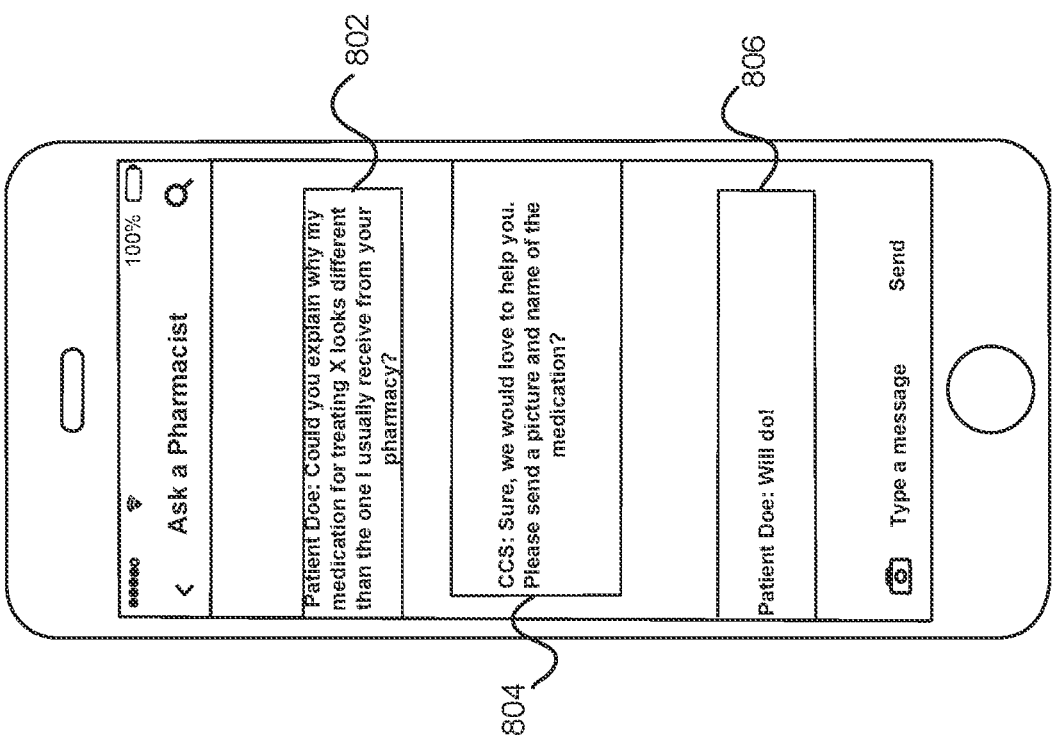

FIGS. 8A and 8B show an example two-way secure communication between the patient and the pharmacy. The communication may take place, for example, after the user is authenticated by signing into the pharmacy application 122 on the patient computing device 116. In FIG. 8A, the patient may have a question 802 regarding a medication and the pharmacy (e.g., via a pharmacist, pharmacy tech, automated response, etc.) provides response 804. The patient may respond to the message 804 with, for example, the message 806. In FIG. 8B, the patient provides a message 808 including a picture and text regarding the question asked in 802 of FIG. 8A and a response 810 is received.

FIGS. 9A-9D show an example flow for authenticating and communicating sensitive information between the patient and the CCS. The illustrated embodiments shown in FIGS. 9A-9D may, for example, be used for the two-way pharmacy-initiated secure communication described above.

In FIG. 9A, the patient receives a message in messaging application 118 on patient computing device 116 from the CCS (e.g., via messaging server 124). The message may include a link 902 which the patient can interact with (e.g., click) to facilitate authenticating the patient to initiate secure communication with the pharmacy. In response to the patient clicking on the link 902, the patient computing device may, in one embodiment, launch pharmacy application 122 to authenticate the user and initiate a secure communication session. As shown in the example of FIG. 9B, in one embodiment, the patient may be authenticated using biometric authentication (e.g., fingerprint authentication, iris detection, facial recognition, or the like).

In FIG. 9C, the patient provides relevant biometric authentication data to the CCS and receives the message shown. The system may further require information from the patient such as insurance data, etc. Thus, the patient may respond as shown in the response provided by Patient Doe in FIG. 9D.

FIG. 10 is an example aggregate of queued messages to be sent to a plurality of patients. In the illustrated embodiment, the messaging module 106 may populate a table with a patient ID, phone number, relevant message, and a transaction ID (campaign ID) associated with the message. As previously noted, the messaging module 106 may transmit the queued message(s) in a single mode (e.g., send a single message to the patient) or in a batch mode (e.g., send a plurality of messages simultaneously to multiple patients), or a combination of both.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions and/or formats.

Furthermore, the modules, routines, features, attributes, methodologies, and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A method comprising:
capturing first patient data by a sensor configured to monitor a state about a first patient;
training, by a computing system, a first instance of a machine learning model profile to identify at least one discrete opportunity to initiate dialogue with the first patient by applying at least one machine learning technique to the first patient data and based on the first patient being associated with a message type;
analyzing, by the computing system, a first patient profile associated with the first patient to determine whether the first patient profile fits the first instance of the machine learning model profile by identifying patterns within the first patient profile that match the machine learning model profile;
in response to determining that a first patient profile fits the first instance of the machine learning model profile, automatically generating, by the computing system, a message corresponding to the message type and based at least in part on the state about the first patient;
automatically, electronically transmitting, by the computing system, a message to a patient computing device of the first patient;
electronically receiving, at the computing system, a first patient response to the message;
retraining, by the computing system, the first instance of the machine learning model profile based on the first patient response to the message, thereby generating a second instance of the machine learning model profile; and
analyzing, by the computing system, a second patient profile associated with a second patient to determine whether the second patient profile fits the second instance of the machine learning model profile by identifying patterns within the second patient profile that match the second instance of the machine learning model profile.

2. The method of claim 1, further comprising:
further training the first instance of the machine learning model profile based on other patient data stored in association with the first patient profile.

3. The method of claim 1, further comprising:
identify, using the second instance of the machine learning model profile, another discrete opportunity to initiate dialogue with the first patient.

4. The method of claim 1, wherein the message is a portion of a two-way secure communication with the first patient including a question for the first patient.

5. The method of claim 4, wherein the computing system authenticates the first patient based on a response from the first patient.

6. The method of claim 1, wherein the computing system retrains the first instance of the machine learning model profile by:
generating an evaluation of a content and context of the response from the first patient; and
incorporating the evaluation into retraining the first instance of the machine learning model profile, thereby generating the second instance of the machine learning model profile.

7. The method of claim 1, wherein the first instance of the machine learning model profile is generated based on one or more patient factors.

8. The method of claim 1, wherein the first instance of the machine learning model profile is generated based on one or more patient factors, the patient factors comprising one or more of:
a demographic factor describing a particular class of patients with shared characteristics to which the first patient belongs to;
a medication intake factor derived from prescription information of the first patient;
a diagnosis factor describing a cause and nature of a medical condition associated with the first patient;
an insurance factor derived from health insurance information associated with the first patient;
a clinical interaction factor describing a nature of historical interactions between the first patient and a care team;
a digital interaction factor describing a digital footprint of interactions between the first patient and the computing system;
a retail purchase history factor associated with the first patient;
a payment history factor describing one or more sources of payment associated with prescription purchases of the first patient; and
a health record factor describing a medical history of the first patient.

9. The method of claim 1, wherein branching and conditional data analysis are applied to a patient response to send a subsequent message from the computing system to the first patient.

10. The method of claim 1 further comprises:
training, by the computing system, the machine learning model profile based on third-party data, the third-party data including captured health data associated with the first patient.

11. A system comprising:
one or more processors; and
one or more memories storing instructions that, when executed, cause the one or more processors to:
capture first patient data by a sensor configured to monitor a state about a first patient;
train a first instance of a machine learning model profile to identify at least one discrete opportunity to initiate dialogue with the first patient by applying at least one machine learning technique to the first patient data and based on the first patient being associated with a message type;
analyze a first patient profile associated with the first patient to determine whether the first patient profile fits the first instance of the machine learning model profile by identifying patterns within the first patient profile that match the machine learning model profile;
in response to determining that a first patient profile fits the first instance of the machine learning model profile, automatically generate a message corresponding to the message type and based at least in part on the state about the first patient;
automatically, electronically transmit a message to a patient computing device of the first patient;
electronically receive a first patient response to the message;
retrain the first instance of the machine learning model profile based on the first patient response to the message, thereby generating a second instance of the machine learning model profile; and
analyze a second patient profile associated with a second patient to determine whether the second patient profile fits the second instance of the machine learning model profile by identifying patterns within the second patient profile that match the second instance of the machine learning model profile.

12. The system of claim 11, wherein the instructions, when executed, cause the one or more processors to:
further train the machine learning model profile based on other patient data stored in association with the first patient profile.

13. The system of claim 11, wherein the instructions, when executed, cause the one or more processors to:
identify, using the second instance of the machine learning model profile, another discrete opportunity to initiate dialogue with the first patient.

14. The system of claim 11, wherein the message is a portion of a two-way secure communication with the first patient including a question for the first patient.

15. The system of claim 14, wherein the instructions, when executed, cause the one or more processors to authenticate the first patient based on a response from the first patient.

16. The system of claim 11, wherein the instructions, when executed, further cause the one or more processors to retrain the first instance of the machine learning model profile by:
generating an evaluation of a content and context of the response from the first patient; and
incorporating the evaluation into retraining the machine learning model profile to identify another discrete opportunity, thereby generating the second instance of the machine learning model profile.

17. The system of claim 11, wherein the machine learning model profile is generated based on one or more patient factors.

18. The system of claim 11, wherein the machine learning model profile is generated based on one or more patient factors, the patient factors comprising one or more of:
- a demographic factor describing a particular class of patients with shared characteristics to which the first patient belongs to;
- a medication intake factor derived from prescription information of the first patient;
- a diagnosis factor describing a cause and nature of a medical condition associated with the first patient;
- an insurance factor derived from health insurance information associated with the first patient;
- a clinical interaction factor describing a nature of historical interactions between the first patient and a care team;
- a digital interaction factor describing a digital footprint of interactions between the first patient and a computing system;
- a retail purchase history factor associated with the first patient;
- a payment history factor describing one or more sources of payment associated with prescription purchases of the patient; and
- a health record factor describing a medical history of the first patient.

19. The system of claim 11, wherein branching and conditional data analysis are applied to a patient response to send a subsequent message from a centralized computing system to the first patient.

20. The system of claim 11, wherein the instructions, when executed, cause the one or more processors to train the machine learning model profile based on third-party data, the third-party data including captured health data associated with the first patient.

* * * * *